(12) United States Patent
Hasel

(10) Patent No.: US 6,315,567 B1
(45) Date of Patent: *Nov. 13, 2001

(54) METHOD OF RESTORING A TOOTH

(75) Inventor: Robert W. Hasel, Lakeland, MN (US)

(73) Assignee: Abco Research, LLC, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/313,850

(22) Filed: May 18, 1999

Related U.S. Application Data

(60) Provisional application No. 08/969,911, filed on Nov. 13, 1997, now Pat. No. 5,944,527, provisional application No. 08/646,707, filed on May 6, 1996, now abandoned, and provisional application No. 08/319,456, filed on Oct. 16, 1994, now Pat. No. 5,547,379.

(51) Int. Cl.[7] ................................ A61C 5/00
(52) U.S. Cl. ............... 433/228.1; 433/226; 433/212.1
(58) Field of Search .................... 433/226, 228.1, 433/80, 89, 90, 212.1

(56) References Cited

U.S. PATENT DOCUMENTS

| | | | |
|---|---|---|---|
| 2,654,948 | * | 10/1953 | Rubin .................. 433/226 X |
| 3,421,222 | * | 1/1969 | Newman ................ 433/226 X |
| 3,914,868 | * | 10/1975 | Schwartz et al. .......... 433/226 |
| 4,297,266 | | 10/1981 | Ibsen et al. . |
| 4,411,625 | | 10/1983 | Koblitz et al. . |
| 4,601,662 | | 7/1986 | Galler . |
| 4,634,383 | * | 1/1987 | Beyer et al. ............... 433/226 |
| 4,648,843 | | 3/1987 | Mitra . |
| 4,696,955 | | 9/1987 | Kuhlmann . |
| 4,707,504 | | 11/1987 | Walkowiak et al. . |
| 4,764,118 | * | 8/1988 | Touati et al. .............. 433/226 |
| 4,859,716 | | 8/1989 | Ibsen et al. . |
| 5,228,907 | | 7/1993 | Eppinger et al. . |
| 5,246,371 | * | 9/1993 | Fischer ................... 433/226 X |
| 5,334,625 | | 8/1994 | Ibsen et al. . |
| 5,547,379 | | 8/1996 | Hasel . |
| 5,587,406 | | 12/1996 | Yamamoto et al. . |
| 5,944,527 | | 8/1999 | Hasel . |

OTHER PUBLICATIONS

Jeneric/Pentron product catalog, Fall/Winter 1993, 4 pages.
Five (5) pages representing the instructions and container of a 1992 Jeneric/Pentron product.

(List continued on next page.)

Primary Examiner—Nicholas D. Lucchesi
(74) Attorney, Agent, or Firm—Dorsey & Whitney LLP

(57) ABSTRACT

A method of restoring a tooth is provided, method comprises the steps of dispensing a curable composition from an applicator and curing the curable composition. The applicator has a needle with a lumen. The composition is injected into a hollow on the tooth to achieve a desired shape. The composition includes curable liquid resin portion and an inorganic filler portion. The curable liquid resin portion has a polymerizable binder resin.

21 Claims, 5 Drawing Sheets

OTHER PUBLICATIONS

Sockwell CL. *The Art and Science of Operative Dentistry*, Chapter 16; Silicate Cement and Self–Curing Acrylic Resin Restorations, McGraw–Hill Book Company 1968;pp.437–477.

Leinfelder, KF and Turner, DT. The Esthetic Restoration of Teeth. *N.C. Dental Journal* Aug. 1971;pp.001–004.

Greener EH, Harcourt JK, Lautenschlager EP. *Materials Science in Dentistry*. Williams & Wilkins Company 1972;pp. 326–335, 340–344.

Kusy, RP, Mahan JR, Turner DT. Influence of Application Technique on Microstructure and Strength of Acrylic Restorations. *J. Biomed. Mater. Res* 1976; vol. 10:77–89.

Advertisement for Ultra–Blend, Ultradent Products Inc. 1989.

Phillips, RW. *Science of Dental Materials, Ninth Edition*, Chapter 12: Restorative Resins, W.B. Sauders Company 1991; pp. 215–248.

Direction For Use: Pentra Seal with Flouride System$^2$. Jeneric/Pentron Incorporated 11/92–5M.

Anusavice, KJ. *Phillips' Science of Dental Materials, Tenth Edition*, Chapter 12 Restorative Resins, W.B. Saunders Company 1996; pp. 273–299.

Correspondence from Department of Health & Human Services, Nov. 18, 1998.

Jeneric/Penetron product catalog, Fall/Winter 1993, 4 pages.

Five (5) pages representing the instructions and container ofa 1992 Jeneric/Pentron product.

* cited by examiner

METHOD OF RESTORING A TOOTH

RELATED APPLICATIONS

This is a continuation application of U.S. application Ser. No. 08/969,911, filed on Nov. 13, 1997, now issued as U.S. Pat. No. 5,944,527, issued on Aug. 31, 1999, which is a continuation of U.S. application Ser. No. 08/646,707, filed on May 6, 1996, now abandoned, which is a coninuation of U.S. application Ser. No. 08/319,456, filed on Oct. 6, 1994, now issued as U.S. Pat. No. 5,547,379, issued on Aug. 20, 1996, which are hereby incorporated by reference in their entirety.

FIELD OF THE INVENTION

The present invention relates to a method for restoring a defect in a tooth by using a curable composite material.

BACKGROUND

Teeth with dental decays such as cavities are generally restored by removing the decayed area and applying a restorative thereon. Traditionally, amalgam material has been used for filling and repairing teeth. Because the amalgam material tends to harden as it is being worked, and its thick, lumpy consistency necessitates using specialized tools for pushing the materials into corners and crevices to facilitate adaptation to the tooth, its use is inconvenient and causes great discomfort to the patient. Moreover, the retention of an amalgam resotative in a tooth is by bulk. For repairing a small decayed area, often an amount of healthy tool structure many times the decayed area has to be removed to provide toom to receive the amalgam material.

The concern of the presence of mercury in amalgam material has led to the introduction of other restoratives that do not contain mercury. For example, "Universal Paste" composites, such as P-SO and Z-100 sold by 3M Company, have been used for restoring teeth. Examples of other composite materials that can be used for repairing teeth include the compositions disclosed in U.S. Pat. No. 4,553,940 (Koblritz, et al) and U.S. Pat. No. 5,228,907 (Eppinger, et al).

Generally, composite materials for repairing teeth are thick and sticky, making them difficult to work with and highly technical skill is required of the operator to properly place such materials in teeth for restoration purposes. Universal paste type composites are generally used by trowelling an amount of the paste into position in a hollow (or void or cavity), tamping the paste down to improve contact with the surface of the cavity, carving the excessive paste into a rough outline of the desired shape, and polishing the cured composite to a desired shape and smoothness.

Because a composite material, similar to amalgam material, is generally applied as a lump in the prepared location in a tooth, voids and porosities are often incorporated into the material during placement because of the difficulty in manipulating the material into corners and crevices in the tooth. Furthermore, if a composite material is light curable, because of the thickness of the composite material applied, incomplete polymerization often results.

Another kind of restorative material that does not contain mercury is a film-forming composition that is generally used as a sealant, glaze, or adhesive. Typically, such a film-forming dental composition contains resins with little or no filler materials. Such filmforming dental compositions are typically used for sealing the tooth against cracks adjacent to fillings. Such compositions generally have low viscosity and can be applied to the tooth by using a brush. An example of a sealant is disclosed in U.S. Pat. No. 4,001,483 (Lee, Jr., et al.). Such a composition is generally applied as a thin coating and when cured, forms a sealing coat on the tooth. Yet another kind of coating composite is used for masking stains and discolorations. For example, U.S. Pat. No. 4,150,485 (Lee, Jr., et al) discloses a brushed on dental restorative coating composition used for covering surface imperfections. This composition has a higher viscosity than conventional sealants. Such film-forming and coating compositions have not been applied in restoration of tooth decays such as filling cavities.

SUMMARY

The present invention provides a method of restoring a tooth that has a defect. The method includes dispensing a curable composition through a needle with a lumen into a hollow on the tooth to achieve a desired shape and curing the curable composition. As used herein, the term "needle" refers to a slender, hollow, stiff instrument which may be straight, curved or bent, with or without a sharp point. The composition contains a curable liquid resin portion and an inorganic filler portion. The curable liquid resin portion has a polymerizable binder resin. As used herein, a "hollow" refers to a void area or cavity that results after a tooth has been prepared to receive a restorative by a cutting or abrasive tool such as a dental bur.

In another aspect, the present invention provides a method of restoring a tooth having a decayed portion including the steps of removing the decayed portion to form a hollow in the tooth, coating the surface in the hollow with a curable bond and curing the bond, dispensing a curable composition from a needle in the hollow to achieve a desired shape, curing the curable composition, and repeating the dispensing of the curable composition and curing the curable composition until a cured structure of desired shape and smoothness is obtained. In removing the decayed portion, an amount of an adjacent healthy portion or the tooth is removed with the decayed portion. The volume of the healthy portion removed is about zero to three times, preferably 0.5 to 3 times the decayed portion. The composition contains a curable liquid resin portion and an inorganic filler portion. The curable liquid portion has a polymerizable binder resin and a polymerizable diluent monomer less viscous than the polymerizable binder resin.

The present invention provides yet another method for restoring a tooth using a composition that contains a curable liquid resin portion and an inorganic filler portion. The method includes the steps of dispensing a curable composition from a needle as one of a layer and a drop in the hollow, curing the curable composition wherein the one of a layer and drop shrinks when it is cured, dispensing the curable composition as one of a layer and drop on top of the cured composition and in the void space resulted from the shrinkage to compensate for the shrinkage, and repeating the dispensing and curing of the composition in the hollow until a cured structure of desired shape and smoothness is obtained. The method of the present invention can be advantageously utilized to restore defects in teeth. Because of the composition of the present invention can be applied using a hypodermic needle like tubular structure, the composition can be applied into a small hollow in hard to-reach places on a tooth. By laying the curable composition as a thin layer or small drop, substantially complete curing by light (as compared to relatively incomplete curing when conventional universal paste-type of composite is used) can be realized. Such substantial complete curing leads to improved mechanical integrity and chemical resistance of the restorative material in the tooth. Better curing leads to less stress cracking taking place in the restorative material.

The use of conventional composite material often leads to a great amount of shrinkage as the material is cured. Such shrinkage can lead to many problems, such as accelerated wear, open margins between the tooth surface and the filling material, leakage of foreign material into the unfilled area, thereby causing degradation and subsequent development of caries. In the present invention, by depositing the composition as thin layers, curing, and repeating the process the void area left by the shrinkage of a previous cured area can be filled with a subsequent layer with the composition, thereby eliminating or greatly reducing the presence of unfilled areas caused by shrinkage.

The thixotropic characteristic of the restorative curable composition of the present invention greatly facilitates the restoration of tooth without having to shape the composition using a scraping tool. The thixotropic substance can be forced through a syringe and needle and carefully deposited in a desired location and cured. By gradually building up the cured structure, there is no need to remove excess composite material to achieve a desired shape. The relatively low viscosity of the composition helps to spread the composition into crevices and corners to greatly reduced amount of void area so that a strong bond can result between the composition and the tooth without depending on retention of the restorative material by bulk. The low viscosity nature of the composition, as compared to conventional universal paste type composites, allows for much less manipulation of each increment placement of the composition. Therefore, manipulation by paddling, pushing or prodding to place and shape the composite material (as in the case of using a universal paste) is not necessary. This makes the composition of the present invention easier and quicker to place and results in a less degree of discomfort to the patient. Because of the affinity of the bond to the composition of the present invention, the composition is further facilitated to flow into crevices and corners it—encounters. A drop (i.e., a dab or a bead) or a thin layer of the composition, when placed in a hollow, such as for Class IV restoration, will not run (i.e., flow or drip out of the hollow under gravity). The surface tension of the thixotropic composition is selected by varying the concentration of the various ingredients in the composition so as to become compatible with the surface of the tooth structure and to provide an affinity to the bond.

The curing of the composition of the present invention provides a smooth surface, thereby eliminating the need for finishing, polishing, and visual inspection of margins. This, and the ability to adhere to a surface of the tooth without depending on bulk, make possible the restoration of a tooth without removing an excess amount of healthy tooth structure as in a case of using amalgam or conventional universal paste-type composite. This affords a great advantage of retaining a significant amount of the healthy tooth structure, thereby reducing a trauma to the tooth and the likelihood of losing the tooth completely through multiple restorative procedures. Contrarily, the prior art methods requires excessive removal of healthy tooth structure. Quite often, because of wear (i.e., abrasion) and bacterial attack through the years, the same tooth needs to be restored many time. With excessive tooth structure removal as in the prior art methods, the tooth may be weakened to the extent that a crown or extraction is required. The method of present invention, being much more conservative in tooth structure removal, greatly reduces the need for such crowns and extractions.

Because no polishing is necessary to smooth the surface of the restorative structure, polishing-induced cracks, fissures, or irregularities are absent on the restorative structure. Such crevices, fissures and irregularities, if present, would increase the porosity of the restorative structure and lead to accelerated degradation and wear. Mechanical polishing results in scratches on the polished surface. Such scratches, even the finest ones, increase the surface area for mechanical and chemical degradation. Such scratches violate the bonding between the affected filler particles and the resin, which eventually lead to the filler particles falling off. The present invention avoids such scratches, resulting in a longer lasting restoration on the tooth.

In the present method, a syringe-type applicator can be used to store and deliver the composition through a needle-type tubular structure to a desired location on the tooth. Therefore, only one instrument (e.g., the applicator with a needle) is needed for delivering and shaping the composition. No separate instruments are needed for performing the storage, delivery and shaping procedures. A single drop of the composition can be placed precisely on a desired location, beads (or drops) of the composition can be deposited in a line in a vertical or horizontal direction, and a large area can be covered with a thin layer of the composition by using the syringe with a needle. Using such an applicator, the surface of a layer of the composition can be stroked in a brush-like fashion to spread out or be teased into a peak. Because of the thixotropic nature of the composition, various shapes can be accomplished by manipulating the composition with the tip of the needle. Such ease of manipulation affords great convenience to the operator in shaping the composition. Alternatively, a desired shape can be achieved by depositing the composition in small increments to build up the cured restorative structure.

Building the restorative structure this way obviate the need to paddle, push or prod the filling material in the hollow as with the prior art method. This further reduces the trauma and discomfort to the patient. Furthermore, because the restorative structure is built in increments and requires less force, the operator (i.e., dentist) has much better control. The method of the present invention, because of its ease of use and not requiring polishing, can also be done faster than prior art methods using amalgam material or universal paste.

By utilizing the method of the present invention, certain types of tooth restoration that have been very difficult to perform can be done relatively easily. For example, a Class IV restoration (See example below) requires the building of tools in the corner of the tooth. Amalgam generally cannot be used for this procedure. Traditional type of paste composite, although can be used, are very difficult to place and form into a desired geometry. When conventional methods are used, voids and porosities often occur and require additional material to cover them. For Class V restorations, amalgam application requires extra retention and undercuts, necessitating excessive tooth structure removal and weakening of the tooth. The use of conventional universal paste composite aces similar problems. Utilizing the method of the present invention, restoration by simply laying the composition at the precise location one layer or one bead at a time and curing renders the procedure relatively easy to perform and result in a structurally sturdy and aesthetically appealing restored tooth.

BRIEF DESCRIPTION OF THE DRAWING

Illustrative embodiments of the invention are shown in the various figures. Throughout the figures, which are not drawn to scale to show details, identical reference numerals refer to identical structural elements, wherein.

DETAILED DESCRIPTION OF THE INVENTION

Figure 1:
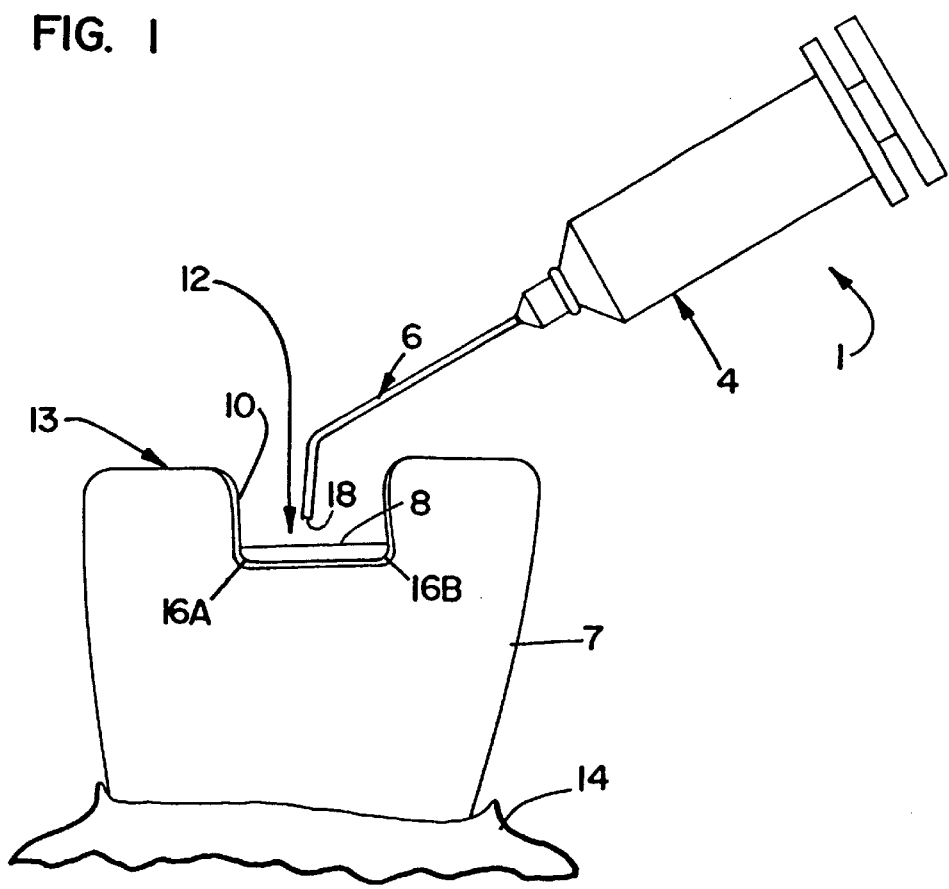
FIG. 1 shows a cross-sectional view of a tooth showing a hollow being restored using a syringe and needle in an embodiment of the method of the present invention.

The present invention utilizes a composition for the restoration of teeth, such as dental fillings for the repair of dental caries.

The Composition

The composition applicable in the present invention includes a curable liquid resin portion containing one or more binder resins and an inorganic filler portion having inorganic fillers. Optional ingredients that can be included in the composition of the present application can include pigments, opacifiers and the like, for improving the aesthetic appearance of the composition after polymerization.

Binder resins are provided in the composition of the present application for binding the various ingredients, including the inorganic fillers so that after polymerization, the composition forms a solid, rigid, mechanically sturdy material effective for sustaining mechanical and chemical challenges which are normally encountered by the load-bearing surface of a tooth. Binder resins suitable for such an application include ethylenically unsaturated polymerizable materials. Preferably, the resin is an acrylated polyester. Such a material may be a monomer, dimer, trimer, and the like that is polymerizable. A preferred material is 2, 2-bis [4(2hydroxy-3-methacryloxypropoxy)phenyl] propane (hereinafter abbreviated as bis-GMA). Another material applicable is polyurethane dimethacrylate (PUDMA). A person skilled in the art would understand that derivatives and polymers and combinations of the above-described materials as well as other materials with similar chemical and physical properties may be utilized as the binder resin in the composition of the present application.

Preferably, the composition applicable in the present invention also includes one or more diluent monomers in an amount effective to render the viscosity of the liquid resin portion (which includes the binder resins and the diluent monomers) low enough to be mixed with the inorganic fillers to provide an injectable composition through a syringe needle. Preferably, the diluent monomer can be mixed with the binder resin to have a Brookfield viscosity of less than 6,000 centipoises (cps) at 25°, more preferably between about 500 and 5,000 cps, more preferably between about 1,000 and 5,000 cps, even more preferably between about 1,000 and 3,000 cps.

The diluent monomer applicable in the present application is polymerizable. Preferably, the diluent monomers are acrylic materials such as 2hydroxyethylmethacrylate (HEMA), ethylene glycol dimethacrylate, diethyleneglycol dimethacrylate, triethylene glycol dimethyacrylate (TEGDMA), trimethylo propane trimethyacrylate, analogous acrylate, and the like. The more preferred diluent monomers are HEMA and TEGDMA.

Other polymerizable material that can be used as monomer or prepolymers to result in a curable liquid portion of appropriate viscosity include methyl methacrylate and bisphenol A dimethacrylate. It is to be understood that a person skilled in the art will be able to device a curable liquid resin portion based on the present disclosure by using the above described or other ingredients. It is believed that a composition can be made with one or more resins that have a viscosity in the range applicable for syringe injection as disclosed in the present disclosure such that the one or more resins can be considered as the binder resin or as the diluent.

The composition of the present invention also contains a catalyst or initiator for initiating the polymerization of the binder resin and the diluent monomer. Preferably, the polymerization of the composition of the present invention in initiated by a initiator system having two components, an alpha diketone photosensitive species and an amine reducing agent. Examples of suitable alpha diketones for initiating polymerization of the composition include camphoroquinone, benzil, biacetyl, 9,10phenanthrenequinone, and naphthoquinone. Of these, the non-aromatic alpha diketones are preferred, camphoroquinone is the most preferred.

A combination of an amine reducing agent with the alpha diketone results in a visible light sensitizing system which is applicable in the composition of the present invention. Amines effective for use in such visible light sensitizing systems include tributylamine, tripropylamine, N-alkyldialkanolamine, tryalkanolamine and acrylate derivatives such as dimethylamino ethylmethacrylate. A preferred amine is methyl diethanolamine. The use of initiators for visible light sensitizing systems in polymerization of tooth restorative composites is known in the art. Further, a person skilled in the art will appreciate that based on the present disclosure, many other binder resins, diluent monomers, alpha diketones, and amines having similar chemical and physical properties as those disclosed above may be utilized in the composition of the present invention.

As previously stated, inorganic fillers are included in the composition of the present invention to impart hardness and durability to the polymerized product. Examples of inorganic fillers suitable for application in the composition of the present invention include barium aluminum silicate, lithium aluminum silicate, strontium, lanthanum, tantalum, glass, silica, quartz, and the like. Preferably, the inorganic fillers are silanated (or silanized) to facilitate bonding with the binder resins. Other suitable inorganic fillers include alumina, zirconia, tin oxide, and titania.

Preferably, the inorganic fillers have a particle size distribution effective for resulting in a cured product having a surface that is smooth compared to surfaces that have been polished by conventional dental restoration technology. Generally particle size ranging from about 0.005 to 15 microns is applicable. Preferred inorganic fillers have a particle size of about 0.01 to 5 microns. The particle size of the inorganic fillers is selected so that the inorganic loading in the compensation is effective to produce a cured product of desired strength, hardness and durability. Inorganic fillers of various types and sizes can be combined (i.e. mixed) to result in a thixotropic composition injectable through a needle.

An inorganic filler that is particularly preferred is fumed silica, which is a colloidal form of silica. Fumed silica generally has a maximum particle size of about 0.05 micron. Although the application of the present invention is not limited by any theory, it is believed that the electron distribution around the colloidal silica facilitates the formation of hydrogen bonding, thereby resulting in a network of loosely attached particles when the colloidal silica is in an appropriate liquid. Therefore, a composition of the present invention containing colloidal silica forms a thixotropic composition. Because of the hydrogen bonding, such a composition is relatively rigid (i.e., viscous). When a stress is introduced into the composition, such as by shearing, the network is broken up partially, resulting in a less viscous composition. The thixotropic characteristic of the composition renders it very useful for application in tooth restoration. The composition can be injected through a long, thin needle such as a hypodermic needle because when pressure is applied by a syringe plunger to force the composition through the needle, the composition becomes less viscous and is dispensed through the exit opening of the needle. However, once disposed at a desired location (for example, as a generally hemispherical dab less than about 5 mm in diameter or a layer less than about 2 mm in thickness) the composition regains its viscous characteristics and will not run (i.e., drip or flow other gravitational pull).

To impact a thixotropic effect to the composition, and yet allow adequate inorganic filler to be incorporated into the curable composition to result in a desired hardness for restoring teeth, fumed silica is preferably incorporated at a concentration of about 30% to 70%, more preferably 40% to 60%, and even more preferably about 50% to 60%, by weight of the inorganic filler material. Generally, particles of larger than 0.05 micron (e.g., about 0.05 to about 5 microns) make up the balance of the inorganic fillers. In a preferred mode, a small amount of the curable composition (for example, a generally hemispherical dab less than about 5 mm in diameter or a layer less than about 2 mm in thickness) can be deposited on the roof of a Class V hollow and yet the composition will not run.

Preferably, the inorganic filler portion is a mixture of inorganic fillers of various particle size and chemical and physical properties to provide hardness and abrasion resistance. For example, barium aluminum silicate glass can be mixed with silicon dioxide, and glass beads of mean particle size of 0.2 to 1 micron can be mixed with glass beads of mean particle size of 0.01 to 0.1 micron. The amount of inorganic fillers that can be incorporated into the curable composition to result in a particular viscosity is affected by the particle size distribution of the filler. Generally, when larger particle size fillers are used, more filler can be incorporated into the curable composition. The ratio can be adjusted to incorporate the desired amount of inorganic fillers in the curable composition for a desired viscosity.

To produce a composition that can result in a cured product of desired mechanical characteristics, the weight ratio of the curable liquid resin portion to the inorganic filler portion is preferably less than 7:3, more preferably less than about 1:1, even more preferably about 3:10 to 1:1, and most preferably about 2:5 to 3:5.

In the curable liquid resin portion, the weight ratio of the polymerizable binder resin to the polymerizable diluent monomer is selected so that the curable liquid portion has a viscosity of less than 6,000 cps at 25° C. and such that the curable liquid resin portion when combined with the inorganic filler portion results in a composition injectable by a syringe through the lumen of a needle such as a hypodermic needle (e.g. 24 gauge needle). Preferably, the weight ratio of the polymerizable binder resin to polymerizable diluent monomer is from about 3:1 to 1:2, more preferably from about 3:2 to 2:3.

The composition of the present invention can be cured by using visible light. Suitable light sources that can be used for curing the compensation is known in art and available commercially. Generally, the polymerization initiating system is added in a quantity sufficient to polymerize a layer of the composition disposed on a tooth in about a few seconds (e.g. 10 seconds) of visible light exposure. Typically, the alpha diketone is added in an amount of about 0.05 to about 0.5 percent of the composition and the reducing amine is added in an amount of about one to five times that of the alpha diketone.

Optional ingredients, such as pigments, opacifiers, brightening agents, and other substances effective for modifying the aesthetic appeal or chemical or physical characteristics of the composition before or after curing can be included in the composition. Although it can be done in a different way, generally, the composition is made by mixing the binder resin and the diluent monomer before the addition of the initiating system components. Subsequent to the addition of the initiating system components, the inorganic fillers and the optional of the ingredients are added and mixed to form the curable composition.

Tables A and B are preferred embodiments illustrative of the composition of the present invention. In Tables A and B, OX-50 is a silanated fumed silica sold by DEGUSSA CORP. BA-30 is barium glass bead filler sold by INDUSTRIAL CORP. GI-2811 is an ionomer resin sold by INDUSTRIAL CORP. The ingredient 077WD (8 p) is a negative expansion filler sold by INDUSTRIAL CORP.

TABLE A

Formulation of Bond

| | |
|---|---|
| Bis GMA | 310 g |
| HEMA | 206 g |
| OX-50 | 70 g |
| BA-30 | 30 g |
| GI-2811 | 25 g |
| Camphoroquinone | 1 g |
| Amine* | 3 g |

*An amine such as methyl diethanolamine was used.

TABLE B

Formulation of Curable Composition for Restoration

| | |
|---|---|
| Bis GMA | 288 g |
| TEGDMA | 288 g |
| OX-50 | 540 g |
| BA-30 | 230 g |
| 077WD (8 μ) | 195 g |
| Camphoroquinone | 1 g |
| Amine* | 3 g |

*An amine such as methyl diethanolamine was used.

The formulations of TABLE A and TABLE B are given as illustrations only. Other polymerizable resins and diluent monomers, as well as inorganic fillers and initiators, as previously disclosed, can be used by a person skilled in the art based on the present disclosure. For example, all the inorganic fillers in TABLE A or TABLE B can be replaced with a 5:1 mixture of silanated glass (e.g. silicon dioxide) beads of mean particle size of about 0.5 micron and silanated glass beads of mean particle size of about 0.05 micron Alternatively, commercially available bonds can be used Also, for the curable composition for restoration, a thicker universal paste type composite material such as P-50 or Z-100 from 3M Co. can be diluted with a diluent such as HEMA or TEGDMA to the desired viscosity. Such a material, although not as preferred as the composition of TABLE B, can be used for restoring teeth with the method of the present invention.

Method of Tooth Restoration

To restore a decayed area in a tooth, first, the tooth is prepared by removing the decayed area. Often only the decayed portion need to be removed. However, if desired, for example, to provide more room for manipulation and inspection, healthy tooth structure less than about 4 times, preferably about 0.5 to 3 times the size of the decayed portion can be removed. More preferably, healthy tooth structure of only 0.5 to 2 times the size of the decayed portion is removed so as to preserve more healthy tooth structure. Subsequently, the surface of the tooth to which the curable composition of the present invention is to be bonded to is coated with a bonding composition (i.e. bond) such as one shown in Table A. Generally, it helps the binder resin (and therefore a curable composition) to bind to the tooth.

Unlike restoration using amalgam which requires bulk to secure the amalgam in place, only a small amount of healthy tooth tissue need be removed along with the decayed portion for receiving the composition of the present invention. Although a large amount of healthy tooth tissue can be removed, preferably, the amount of healthy tooth tissue removed is one to three times the size of the decayed portion. For example, when removing the decayed portion one cubic millimeter of tooth is removed, to prepare the tooth for receiving the curable composition, only an additional one to three cubic millimeter of healthy tooth structure adjacent to the decayed portion is removed. Furthermore, in removing tooth structure to prepare for receiving the curable composition of the present invention, unlike using amalgam or thick semisolid, conventional composite material, it is not necessary to create a hollow of excessively irregular shape or having a large opening leading into an even larger internal volume of hollow.

After a hollow has been prepared on the tooth to receive the composition, the surface of the tooth in the hollow is prepared by etching with a suitable etching solution such as a 10–35 weight percent phosphoric acid. Such etching procedures are known in the art. The etched surface of the tooth is then washed, dried and coated with a bond, which is then cured. These steps, including the application of the bond and the curing thereof can be done with conventional procedures. A bond such as "SCOTCHBOND™" sold by 3M Co. can be used. However, because of the better chemical and physical compatibility with the restorative curable composition of the present invention, the bond of Table A is preferred. Referring to FIG. 1, a curable composition of the present invention can be applied by using an applicator 1 with a needle like tubular structure, e.g., a conventional syringe 4 with a hypodermic needle (for example, a bent 24 gauge lour-lock needle 6 for delivery onto the tooth. Preferably the needle has a bend to facilitate delivery of the composition around a corner. However, needles of other size can also be used (e.g. 25 gauge to 16 gauge), depending on the preference of the operator (i.e., dentist).

The composition (preferably a thixotropic composition) is preferably delivered as a thin layer 8 (i.e., less than 2 mm thick) or a drop (preferably less than five millimeter in diameter) on the bond 10 in the hollow 12 which is on the occlusal side 13 opposite the gum 14. Because of the infinity of the bond 10 for the binder resins in the composition, the composition penetrates crevices and corners 16A, 16B readily. Furthermore, the compensation can be manipulated by the tip 18 of the needle 6 to spread out in the hollow or to achieve a specific desire to shape.

If the hollow 12 is large, more than one layer 8 or drop of the composition may have to be applied. Before the application of another layer or drop of the composition, the first layer or drop is cured by a radiation with a suitable light source (not shown).

Figure 2:
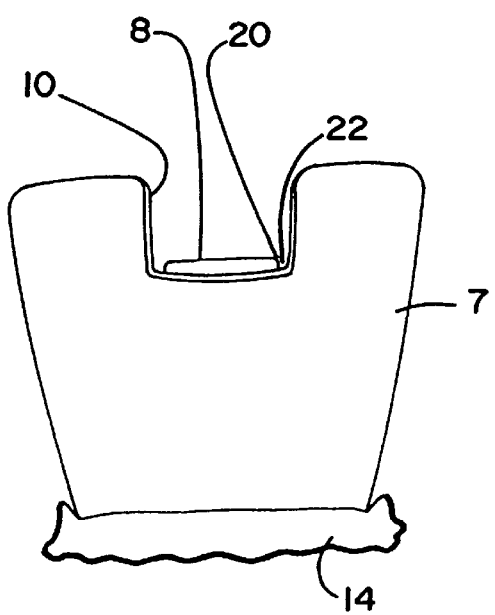
FIG. 2 is a cross-sectional view of a tooth showing a hollow being restored with a further step of the embodiment of the method of FIG. 1.
Figure 3:
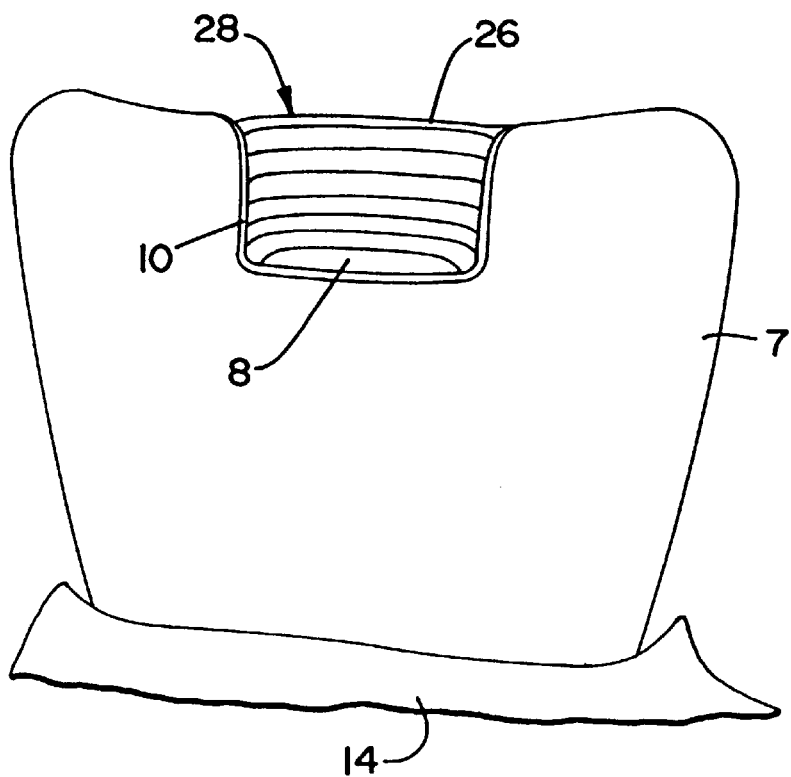
FIG. 3 is a cross-sectional view of a tooth after restoration with the embodiment of the method of FIG. 1.

Referring to FIG. 2, after curing, it is possible that the first layer or drop of composition might have shrunk a little. If this happens, when a second layer or drop of the composition is applied, it is applied or spread to cover the edge 20 of the first layer 8 or drop so that any crevice or void 22 formed by the shrinkage of the first layer is filled. The second layer or drop of the composition is then cured. This process is repeated until the hollow in the tooth is completely filled and the composition manipulated or shaped to achieve a desired shape on the tooth (see FIG. 3). Shaping of the composition by laying the composition and manipulating with a tip of the needle is possible because the viscosity of the composition before curing is such that when applied in a volume as described above, the composition can maintain a shape against the pull of gravity.

Generally, the outermost layer 26 of the composition on the tooth 7 is shaped so that it conforms to the shape of the tooth and such that its surface 28 is smooth. Typically, after curing, the surface 28 of the restorative material is smooth and does not require polishing.

However, if desired, the surface of the restorative material after curing can be polished and glazed to result in a smooth surface. For example, if for any reason (such as overfilling by mistake) the surface of the restorative material needs to be polished, after polishing, the surface is cleaned, etched with an etching solution, washed and dried. A small amount of the composition can be placed on the affected area, brushed to obtain a smooth surface and cured. If there is any voids, porosities, shrinkage areas, or gaps in the margin (i.e. the area between the restorative material and the tooth), they can be filled and sealed with the composition as described to obtain a smooth surface. Because of the presence of a substantial amount of the inorganic filler material, the cured glaze (i.e. composition) in the method of the present invention, unlike prior art bonds and sealants, is very abrasion-resistant.

The following examples illustrate the application of the composition and methods of the present invention in the restoration of defects in teeth.

EXAMPLE 1

Figure 4:
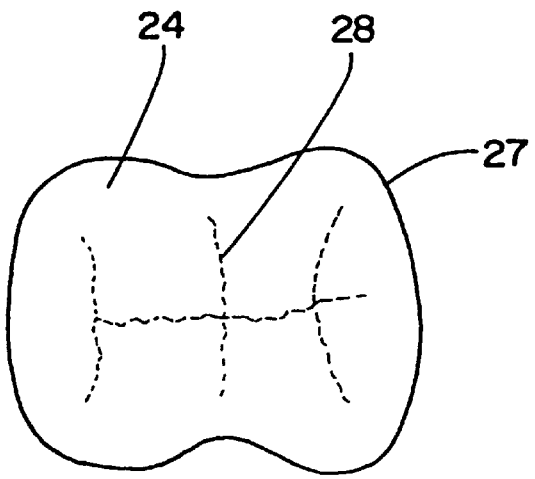
FIG. 4 is a schematic top view of a tooth after a Class I sealant restoration.

The composition according to Table B was applied to a tooth as a sealant. The occlusal pits and grooves of the tooth were slightly manipulated with a rotating diamond instrument to clean the tooth and increase the surface area. The surface of the tooth to be sealed was then prepared with a phosphoric acid solution. After etching, the phosphoric acid was washed from the tooth and the tooth was dried and coated with the bond according to Table A by brushing. The composition according to Table B was applied by means of a syringe through a 24 gauge needle having a bent body without a sharp point (as shown in FIG. 1) into the pits and grooves of the tooth. The composition was then cured by a radiation with a visible light source (e.g., light of 484 nanometer wavelength from a halogen light source). Referring to FIG. 4, a smooth layer of sealing coating 24 was formed on the tooth 27 covering the grooves 28 and crevices (not shown).

EXAMPLE 2

Figure 5:
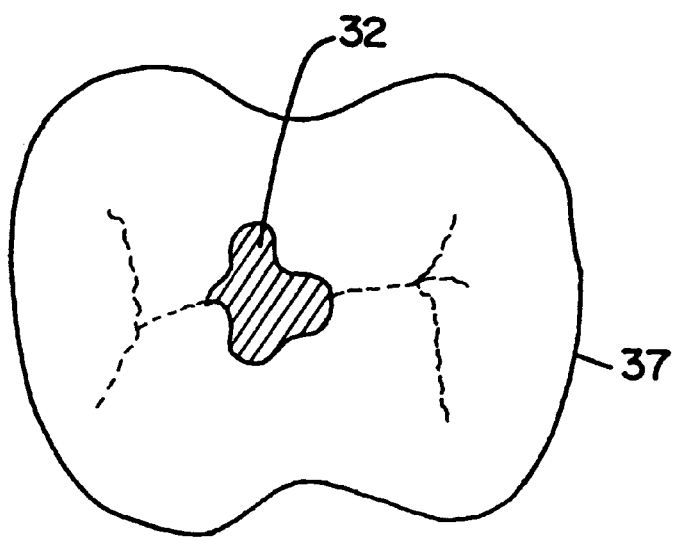
FIG. 5 is a schematic top view of a tooth after a Class I filling restoration.

A Class I restoration was done with a composition according to Table B. The area of the caries in the tooth was removed until healthy tooth structure was exposed without any decayed structure remaining thereon. At this point, no further amount of healthy tooth structure was removed. The occlusal surface of the tooth was then prepared as in Example 1 with etching and coating with the bond. The composition according to Table B was then applied using a syringe with a 24-gauge needle similar to that of Example 1 so that the composition flowed into the prepared area to fill the pits and grooves as well as the area where the caries had been. Referring to FIG. 5, the amount of filling material 32 was small compared to the tooth 37.

EXAMPLE 3

Figure 6:
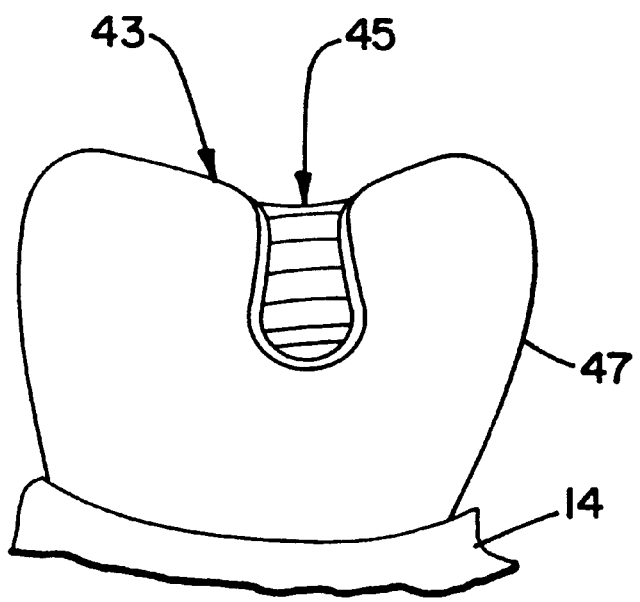
FIG. 6 is a schematic cross-sectional view of a tooth after a Class II filling restoration.

The composition according to Table B was used to restore a Class II cavity. The decayed area of the tooth was removed so that the tooth structure was exposed without any decay structure remaining at this point, no further healthy tooth structure was removed. There was no need to extend the-preparation margins (i.e., the margins of tooth structural removal) to the lingual and buccal aspects of the tooth to provide room for placement of restorative material and for visual inspection of the finished restoration. After the removal of decayed structure, the tooth was further prepared by etching and the application of a bond in a manner similar to Examples 1 and 2. The composition according to Table B was applied by a syringe through a 24-gauge needle similar to that of Example 1 into the hollow resulting from the removal of decayed structure. A thin layer (less than two millimeter thick) of the composition was layered on the surface at the bottom of the hollow. The composition was manipulated with the tip of the needle to spread the composition into any crevice or corner in the hollow. The thin layer of compensation was then cured by irradiation with visible light in a manner similar to the above examples. Subsequently a thin layer of the composition was applied on top of the first layered and manipulated with the tip of the needle so that any groove or crevice in the hollow or resulting from shrinkage of the first layer was filled with the composition. The second layer was then cured by radiation with visible light. This process of laying and curing by a radiation was repeated until the hollow in the tooth was completely filled. The layers were manipulated before curing so that the restorative structure had a desired shape conforming to the original shape of the tooth. Referring to FIG. 6, the filling 45 was disposed on the occlusal side 43 of the tooth 47 opposite the gum 14. The amount of filling material was small compared to the tooth.

EXAMPLE 4

Figure 7:
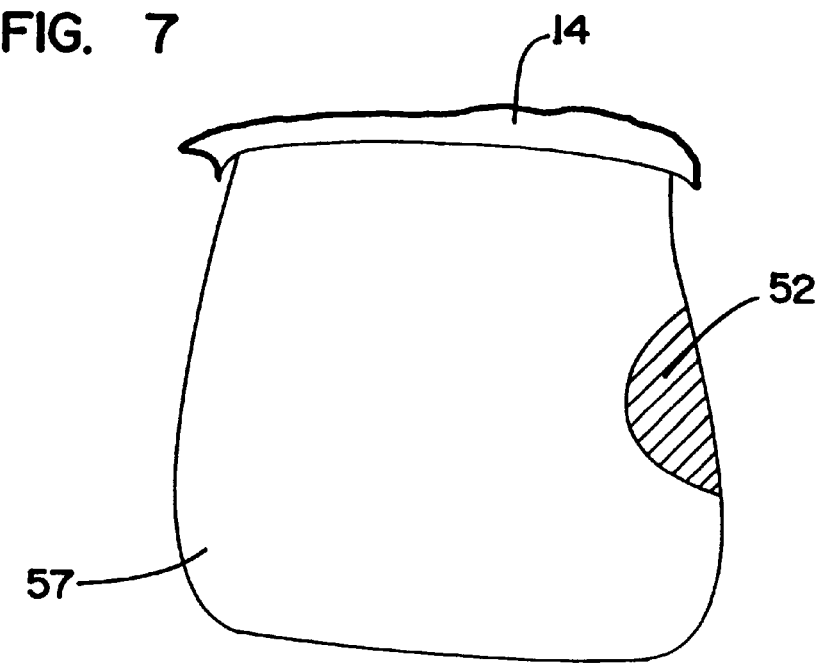
FIG. 7 is a schematic front view of a tooth after a Class III filling restoration.

The composition of Table B was used to repair a Class III cavity. The decayed area in the tooth was removed, etched and coated with a bond in a manner similar to the above examples. The composition of Table B was layered and cured in the hollow using a 24-gauge needle similar to that of Example 1 in a manner similar to Example 3. However, because gravitational force tends to pull the composition downward, the layering was done to gradually build up the restorative structure without the composition running out of the hollow to result in a shape that requires removal of excessive restorative material by abrasion after curing. Referring to FIG. 7, the amount of filling material 52 was small compared to the tooth 57.

EXAMPLE 5

Figure 8:
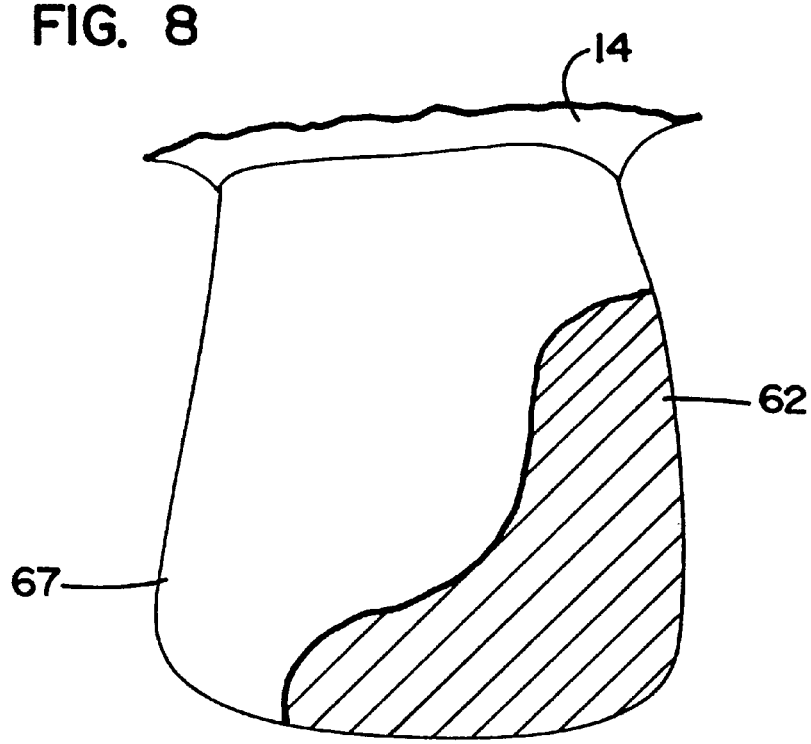
FIG. 8 is a schematic front view of a tooth after a Class IV filling restoration.

The composition according to Table B was used to restore a Class IV defect. The tooth was prepared by removing decayed structure, etching and coating with a bond in a manner similar to the above examples. A thin layer of the composition according to Table B was applied to the prepared surface of the tooth by using a syringe and a 24 gauge needle similar to that of Example 1 and cured. Subsequently, additional layers of the composition were applied to the tooth, shaped by manipulation with the syringe needle, and cured by exposure to visible light so that the final restorative structure conformed to the shape of the original tooth. During the restorative procedure, some of the composition was applied as thin layers and some as small drops so that a desired shape was achieved. Referring to FIG. 8, the amount of filling material 62 was about 30% the volume of the normally shaped tooth 67.

EXAMPLE 6

Figure 9:
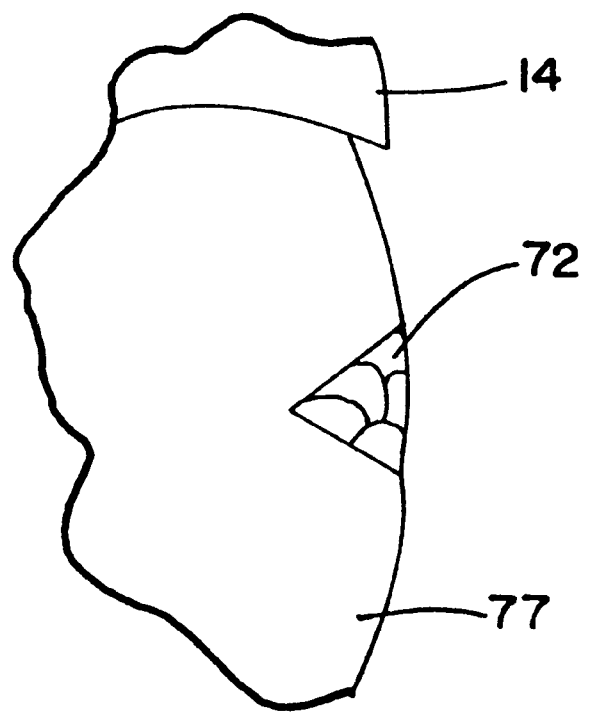
FIG. 9 is a schematic cross-sectional view of a portion of a tooth after a Class V filling restoration.

The composition according to Table B was used for restoring a Class V defect. The decayed tooth structure was removed, etched and coated with a bond in a manner analogous to the above examples. Thin layers or beads of the shaped composition according to Table B were laid using a syringe with a 24 gauge needle similar to that of Example 1, shaped and cured by exposure to visible light one at a time until the hollow was filled and a desired shape conforming to the original shape of the tooth was formed. The composition according to Table B was applied as a dab (or drop) on the bottom (i.e. upwardly facing) surface of the hollow. Because of its thixotropic nature, the composition will not drip or run out of the hollow. The drop of the composition was then cured by exposure to visible light in a manner similar to the above examples. Subsequently, another drop of the composition was placed in the hollow adjacent to the first drop and cured. The process was repeated by building up the restorative structure without leaving unfilled space in the hollow or the composition running out of the hollow. The restorative structure was shaped by manipulating the drops with the—needle in appropriate locations in the hollow to result in a lateral surface that conforms to the surface of the original tooth. FIG. 9 shows the cured drops 72 of the composition in the hollow of the tooth 77.

The present invention has been described in the foregoing specification. The embodiments are presented for illustrative purposes and are not to be interpreted as unduly limiting the scope of the invention. It is to be understood that modifications and alterations of the invention, especially in size and structure or in substitution of similar ingredients in the composition, will be apparent to those skilled in the art without departing from the spirit in scope of the invention. For example, instead of utilizing photosensitive initiators for curing the polymerization of the composition, initiators that cause polymerization without the presence of light can be used. Furthermore, instead of using a syringes, other means of forcing a thixotropic composition through a needle-type lumen can be used. Also, instead of a constant-diameter hypodermic-needle-like instrument, an instrument with a small diameter needle-like tube at an end thereof for position of the composition may be used. All proportions and percentages described herein are in weight unless specified otherwise.

What is claimed is:

1. A method for restoring a tooth, comprising:
   (a) applying a bead of a thixotropic restorative composition to a desired location of the tooth with a syringe-type applicator having a tip;
   (b) manipulating the thixotropic restorative composition with the tip of the syringe-type applicator into a desired shape;

(c) curing said thixotropic restorative composition; and (d) repeating acts (a) through (c) to achieve a cured restorative structure of a desired shape on the tooth.

2. The method of claim 1 wherein the act of curing said restorative composition comprises light-curing said restorative composition.

3. The method of claim 1 further comprising preparing the surface of the tooth by etching with an etching solution.

4. The method of claim 1 wherein the bead of the thixotropic restorative composition is laid as a dab of less than about 5 mm in diameter.

5. The method of claim 1 wherein said thixotropic restorative composition has a viscosity sufficiently high so that a dab of said thixotropic restorative composition less than about 5 mm in diameter or a layer less than about 2 mm in thickness will not run.

6. A method for restoring a tooth comprising:

(a) preparing a cavity using a bur to create a hollow;

(b) applying a thixotropic restorative composition to the hollow using a syringe-type applicator having a tip, wherein said thixotropic restorative composition is applied in a layer less than 2 mm in thickness;

(c) curing the thixotropic restorative composition; and (d) repeating steps (a) through (c) until a desired shape on the tooth is formed.

7. The method of claim 6 including repeating steps (a) through (c) until said hollow is filled.

8. The method of claim 7 wherein said thixotropic restorative composition has a viscosity sufficiently low to flow through said lumen during application to said hollow and a viscosity sufficiently high to not run after application to said hollow.

9. The method of wherein said cavity is one of a Class I, Class II, Class III, Class IV and Class V cavity.

10. A method for restoring Class I through Class V cavities comprising:

preparing one of a Class I through Class V cavity for receiving a restorative composition;

applying the restorative composition directly to the prepared cavity using a syringe-type applicator having a tip;

manipulating the applied restorative composition with the tip of said syringe-type applicator into a desired shape; and curing said restorative composition.

11. The method of claim 10 wherein curing said restorative composition comprises light-curing said restorative composition.

12. The method of claim 11 wherein preparing the cavity further comprises using a bur to create a hollow for receiving the restorative composition and applying the restorative composition further comprises applying the restorative composition to said hollow.

13. The method of claim 12 wherein preparing said one cavity further comprises etching the surface of said hollow; and adding a bonding material to said hollow, wherein said bonding material helps to secure the restorative composition to the hollow after the restorative composition has been applied.

14. The method of claim 13 wherein the tip includes a needle with a lumen.

15. The method of claim 11 wherein said restorative composition is a thixotropic composition having a viscosity sufficiently high after application to said hollow so that said restorative composition will not run, but sufficiently low during application to said hollow so that said composition can be applied via said syringe-type applicator.

16. The method of claim 15 wherein applying the restorative composition further comprises applying the composition in one or more layers, each less than about 2 mm in thickness.

17. A system for restoring a Class I through Class V dental cavity comprising:

a syringe-type applicator having a lumen; and a thixotropic restorative composition in said applicator for application to the hollow of a prepared said cavity through said lumen, wherein the thixotropic restorative composition has a viscosity sufficiently low to allow said thixotropic restorative composition to pass through said lumen when application pressure is applied and sufficiently high to prevent said thixotropic restorative composition from running after application to said hollow, the thixotropic composition comprising a curable liquid resin portion and an inorganic filler portion.

18. The system of claim 17 wherein said applicator includes a needle with a bend and wherein said needle includes said lumen.

19. The system of claim 17 wherein the syringe-type applicator includes a 16 gauge to a 25 gauge needle.

20. A method for restoring a Class I through Class V dental cavity comprising (a) preparing the cavity by forming a hollow in the tooth said hollow having a restorative receiving surface for receiving a restorative composition;

(b) dispensing a bead of a thixotropic restorative composition to the restorative receiving surface with an applicator having a needle-like tubular structure, wherein the needle-like tubular structure has a bend to facilitate precise delivery of the restorative composition;

(c) curing said restorative composition; and (d) repeating steps (a) through (c) until a desired shape is formed on the tooth.

21. The method of claim 20 wherein the bead of thixotropic restorative is less than about 2 mm thick.

* * * * *

UNITED STATES PATENT AND TRADEMARK OFFICE
CERTIFICATE OF CORRECTION

PATENT NO.     : 6,315,567 B1
DATED          : November 13, 2001
INVENTOR(S)    : Robert W. Hasel Page 1 of 1

It is certified that error appears in the above-identified patent and that said Letters Patent is hereby corrected as shown below:

<u>Column 13,</u>
Line 34, please delete "of claim wherein" and insert -- of claim 8 wherein -- therefor.

Signed and Sealed this

Fourteenth Day of May, 2002

Attest:

JAMES E. ROGAN
*Attesting Officer*    *Director of the United States Patent and Trademark Office*

UNITED STATES PATENT AND TRADEMARK OFFICE
CERTIFICATE OF CORRECTION

PATENT NO.   : 6,315,567 B1
DATED        : November 13, 2001
INVENTOR(S)  : Robert W. Hasel It is certified that error appears in the above-identified patent and that said Letters Patent is hereby corrected as shown below:

<u>Column 13,</u>
Line 25, please delete "(a)" and insert -- (b) -- therefor.
Line 27, please delete "(a)" and insert -- (b) -- therefor.

<u>Column 14,</u>
Line 52, please delete "(a)" and insert -- (b) -- therefor.

Signed and Sealed this

Twelfth Day of November, 2002

*Attest:*

*Attesting Officer*

JAMES E. ROGAN
*Director of the United States Patent and Trademark Office*